United States Patent [19]

Levine

[11] Patent Number: 5,406,965
[45] Date of Patent: Apr. 18, 1995

[54] DEVICE AND METHOD FOR DENTAL FLOSSING

[76] Inventor: Steven K. Levine, 39 Gramercy Park North, Apartment 6C, New York, N.Y. 10010

[21] Appl. No.: 93,419

[22] Filed: Jul. 19, 1993

[51] Int. Cl.⁶ ............................................. A61C 15/00
[52] U.S. Cl. ................................................... 132/323
[58] Field of Search .............. 132/323, 324, 325, 326, 132/327, 321, 329

[56] References Cited

U.S. PATENT DOCUMENTS

| | | |
|---|---|---|
| D. 265,515 | 7/1982 | Levine . |
| D. 272,565 | 2/1984 | Levine . |
| D. 276,378 | 11/1984 | Levine . |
| D. 322,491 | 12/1991 | Huskey . |
| 1,091,789 | 3/1914 | Andren . |
| 1,217,264 | 2/1917 | Baxter . |
| 2,467,221 | 4/1949 | Pastl . |
| 2,648,341 | 8/1953 | Moll . |
| 2,664,093 | 12/1953 | Carpenter . |
| 2,784,722 | 3/1957 | Chamberlin et al. . |
| 2,837,098 | 6/1958 | Sorboro . |
| 3,393,687 | 7/1968 | Whitman . |
| 3,472,247 | 10/1969 | Borsum et al. . |
| 3,631,869 | 1/1972 | Espinosa ........................... 132/323 |
| 3,718,146 | 2/1973 | Myers . |
| 3,734,107 | 5/1973 | Thierman . |
| 3,799,177 | 3/1974 | Bragg . |
| 3,834,404 | 9/1974 | Chien . |
| 3,939,853 | 2/1976 | Spanondis . |

FOREIGN PATENT DOCUMENTS 2122495 1/1984 United Kingdom .

Primary Examiner—Gene Mancene
Assistant Examiner—Nicholas D. Lucchesi
Attorney, Agent, or Firm—Stroock & Stroock & Lavan

[57] ABSTRACT

The present invention relates to an improved device and method for flossing teeth. The device has a handle portion and a finger portion. The finger portion is inserted into an individual's mouth, and the handle portion is used for holding the dental flossing device. In a first embodiment, the dental flossing device has two apertures spaced along the finger portion. The flossing material is threaded through the first aperture and then the second aperture. A user presses one end of the flossing material against the device to keep the flossing material taut. The other end of the flossing material, extending from an aperture at the distal end of the device, is held by the user's fingers or is wrapped around a finger, depending on the individual's personal technique. Thereafter, the finger portion of the device is inserted into the mouth and flossing is performed. In a second embodiment, the device has only a single aperture through which the floss is threaded, a section of the floss being held against a side of the device by the hand of the user during use.

39 Claims, 3 Drawing Sheets

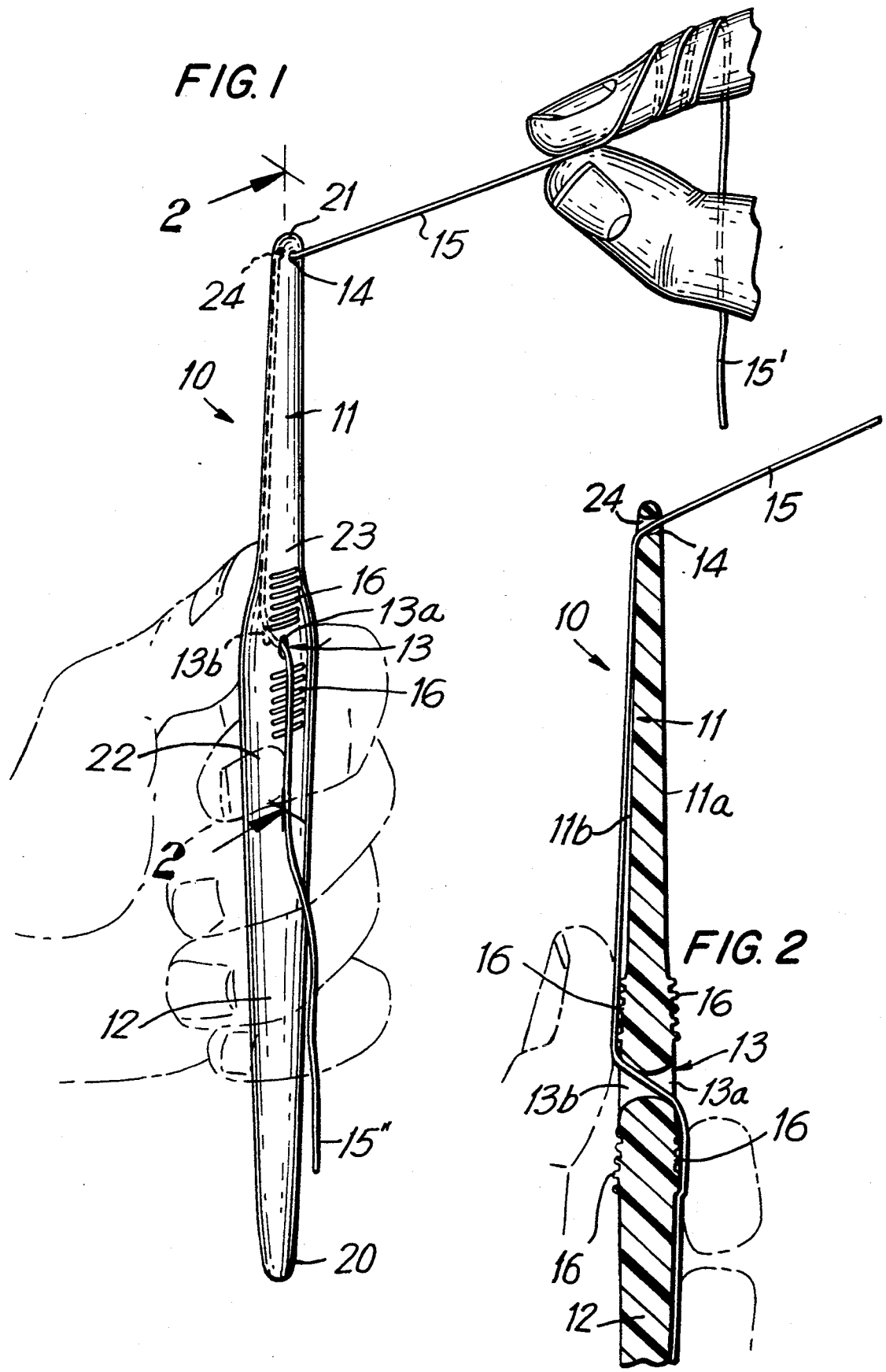

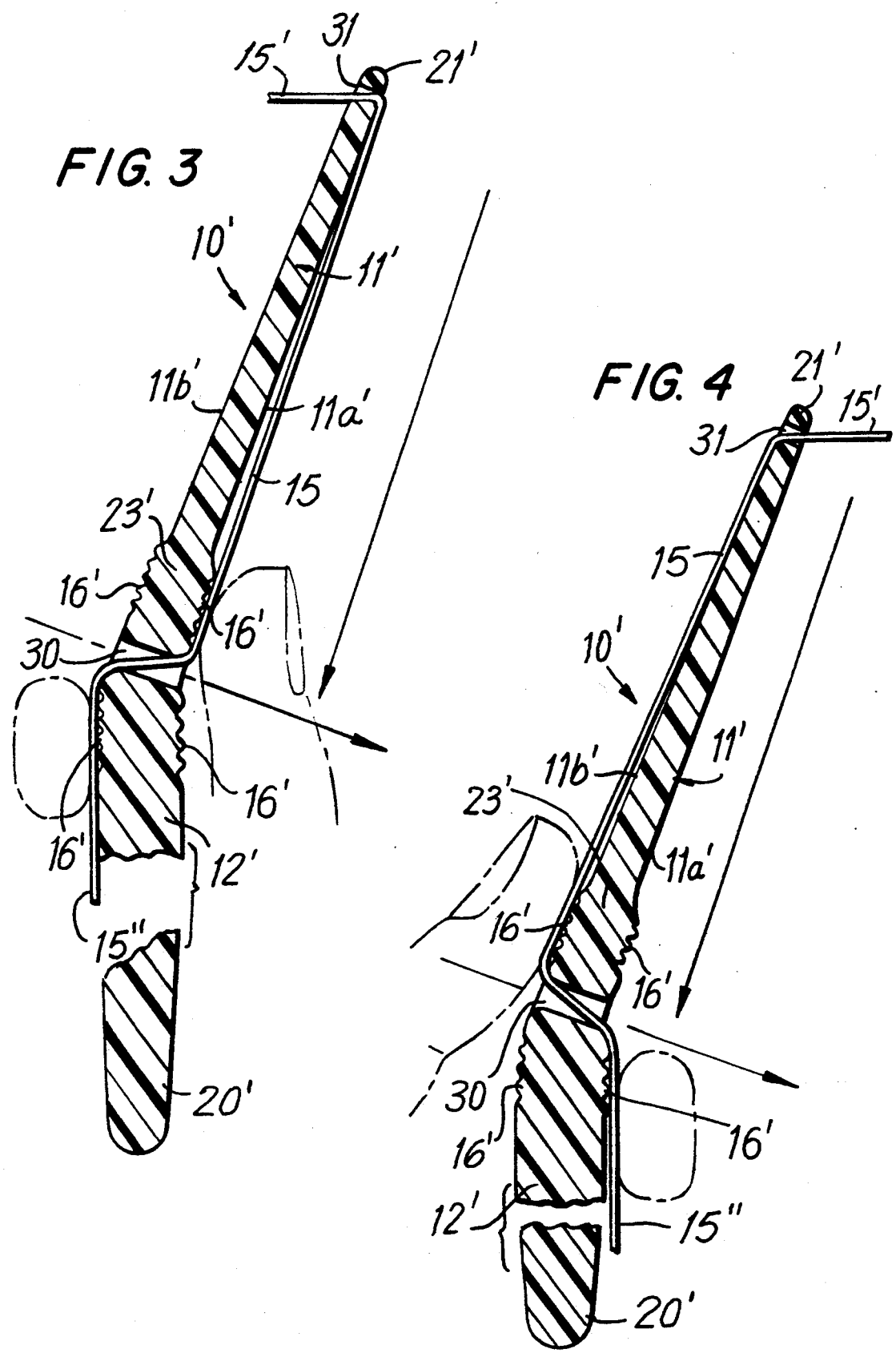

DEVICE AND METHOD FOR DENTAL FLOSSING

BACKGROUND OF THE INVENTION

The present invention relates generally to a device for flossing teeth and, in particular, a device for improving the ability of a person to extract food and other particles from between teeth and to aid in the prevention of infections, diseases, tooth decay and other problems associated with poor dental hygiene.

In the past, devices for flossing one's teeth have been very complicated, having handles which contain a spool of dental floss therein, the floss being fed through a shaft and pulled off the spool through an aperture at the tip of the shaft. Such inventions are disclosed in U.S. Pat. Nos. 3,734,107, 4,434,807 and U.S. Pat. No. Des. 322,491. However, these types of dental flossing devices have numerous drawbacks. Specifically, dental floss must be purchased which is adapted for the specific dental flossing device being used. Furthermore, these devices can be relatively expensive as well as relatively bulky, and therefore difficult to carry for use when needed, such as after meals.

Other dental flossing devices comprise fork-like prongs separated a distance sufficient to contain therebetween a section of dental floss. However, one problem with these devices is the inability to obtain the necessary range of movement within one's mouth. Furthermore, a user may have trouble reaching deep within the back of the mouth with these devices. Another defect in such devices is the need to remove such devices from the mouth and reset a new length of floss when a change in floss is desired or the floss breaks. A representative selection of these devices can be seen in U.S. Pat. Nos. 3,939,853; 3,799,177; 3,472,247; 3,734,107; 3,834,404; 2,837,098; 2,784,722; 2,467,221; 1,217,264 and 1,091,789.

Flossing tools have also been formed of a single member but including means for securing one end of the floss to the tool by means of a knot, or a knob about which the floss can be wrapped. Examples of such devices include U.S. Pat. Nos. 3,393,687; 1,890,788; U.S. Pat. Nos. Des. 272,565; 265,515 and 276,378. However, those devices have the drawbacks of requiring removal from the mouth and manipulation to advance a fresh length of floss. This increases the time required for flossing and complicates use.

Still another variation on flossing tools also involves the use of a single device bent at its end to provide two points for securing a length of floss therebetween. Examples of these tools include U.S. Pat. Nos. 2,664,093 and 2,648,341.

Accordingly, it is desired to provide an improved flossing device for flossing one's teeth having a construction which will allow a user to more efficiently floss, as well as providing the easiest transition from using only one's fingers to using the present invention, regardless of an individual's personal flossing techniques.

SUMMARY OF THE INVENTION

Generally speaking, in accordance with the present invention, an improved dental flossing device is provided including an elongated stick member having a handle portion and a finger portion, the handle portion having a first end and a second end and the finger portion having a near end and a free end, with the near end of the finger portion connected to the second end of the handle portion. The stick member has a first aperture for receiving a piece of dental floss, the aperture positioned essentially near the connection of the near end of the finger portion and the second end of the handle portion. The stick member also has a second aperture for allowing a selected length of floss to pass therethrough. This aperture is positioned essentially at the free end of the finger portion. The first and second apertures extend essentially orthogonally to the longitudinal axis of the portion of the stick member through which it passes. In use, the user threads the selected length of floss through one of the first or second apertures into the other of the first or second apertures, so that a portion of the floss extends along one side of the finger portion between the apertures and a desired length of the floss terminating in a free end extends from the second aperture for manipulation by a first hand of the user. The user can fix the position of the selected length of floss relative to the stick member by exerting pressure on a portion of the floss against the stick member by the second hand. The user can hold the stick member by the handle portion so as to permit a digit(s) of the second hand to press the floss against the handle portion, the finger portion, or the entrance to the first aperture. The end of the dental floss that exits the second aperture is held by either a plurality of fingers or by wrapping the dental floss repeatedly around a finger of the user's first hand, and by creating tension on the dental floss, the desired length of dental floss between the user's first hand and the stick member is thereby kept taut. The finger portion then penetrates into the user's mouth and by using a back and forth motion or an up and down motion, or the like, food particles or plaque will be more readily dislodged. When a fresh length of floss is needed, all that is required is to release the pressure on the floss at or near the first aperture, pull the desired length of floss by using the first hand and reapplying pressure on the floss at or near the first aperture by a digit(s) of the user's second hand.

In an alternative embodiment, the finger and handle portions of the stick member are at an obtuse angle to each other. In still another embodiment only a single aperture is provided at the free end of the finger portion extending orthogonally to the longitudinal axis of the finger portion.

Accordingly, it is an object of the present invention to provide an improved dental flossing device and method.

Another object of the present invention is to provide an improved dental flossing device having a construction that will improve the reach of the dental floss into the user's mouth.

Another object of the present invention is to provide an improved dental flossing device and method having a construction that is easy to use and facilitates a user's transition from only using one's fingers to using the present invention.

Still another object of the present invention is to provide an improved dental flossing device having a construction that will help prevent gum disease by plaque removal, tooth decay, and gingivitis.

Still other objects and advantages of the invention will in part be obvious and will in part be apparent from the specification.

The invention accordingly comprises the features of construction, combination of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of a dental flossing device in accordance with a first embodiment of the present invention;

FIG. 2 is a fragmentary cross-sectional view taken along line 2—2 of FIG. 1;

FIG. 3 is a fragmentary cross-sectional view in accordance with a second embodiment of the present invention;

FIG. 4 is a fragmentary cross-sectional view in accordance with the second embodiment of the present invention showing an alternative method of using the flossing device.

DETAILED DESCRIPTION OF THE PREFERRED EMBODIMENTS

Figure 5:
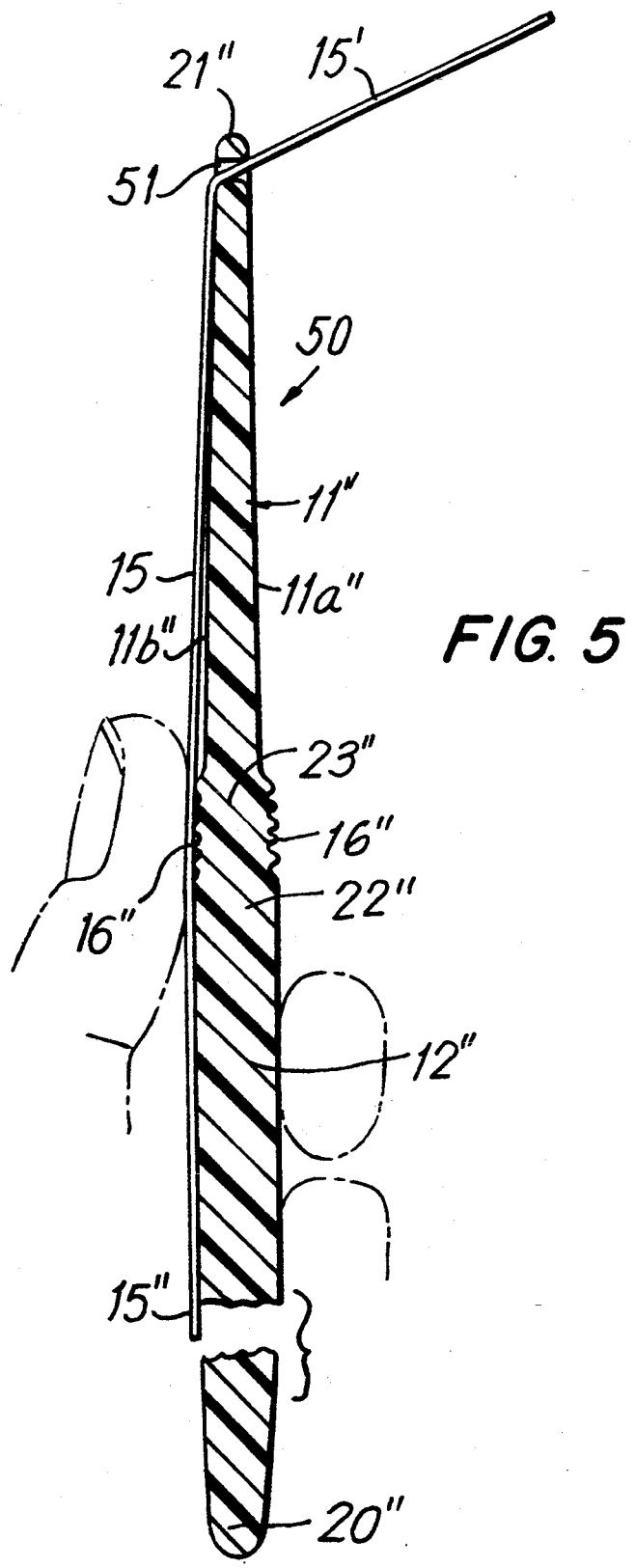
FIG. 5 is a cross-sectional view of a dental flossing device in accordance with a third embodiment of the present invention.

Reference is made to FIGS. 1 and 2 which illustrate a first embodiment of the apparatus for dental flossing of the present invention.

A dental flossing device for flossing, designated generally at 10, has a handle portion 12 and a finger portion 11. Handle portion 12 has a first end 20 and a second end 22. Finger portion 11 has a free end 21 and a near end 23. Near end 23 of finger portion 11 is joined to second end 22 of handle portion 12. In a preferred embodiment, flossing device 10 is made from a molded plastic such as polyurethane but it is understood that the device according to the present invention could also be made from wood, rubber, metal or other suitable hard materials.

Handle portion 12 is tapered from second end 22 to first end 20 of flossing device 10. Finger portion 11 is also illustrated as sharply tapered adjacent its near end 23 and then more gradually tapered as one approaches free end 21. However, flossing device 10 can also be designed such that only handle portion 12 or finger portion 11 is tapered, or neither handle portion 12 or finger portion 11 is tapered, thereby giving flossing device 10 a more rectangular shape.

However, the tapering of the handle portion 12 allows for a more comfortable grip and the tapering of finger portion 11 allows for easier penetration inside of the mouth and manipulation within the mouth. A further advantage of providing a major portion of finger portion 11 extending to the free end with a smaller cross-sectional area than both the junction between the finger and handle portions and most of the length of the handle portion, is that it permits the finger portion to flex to relieve tension on the floss when pulled. The thinness of handle portion 12 is constrained by comfort concerns and the thinness of the finger portion 11 is constrained primarily by the diameter of a second aperture 14 at the free end 21 and the minimum strength requirements for the finger portion. The smaller the diameter of second aperture 14, the more difficult it is to thread the floss therethrough.

The cross-sectional shape of flossing device 10 can be round, elliptical, or of any convenient shape that preferably does not have sharp edges on which the user could cut his or her mouth.

A key feature of the present invention is the utilization of only two apertures, a first aperture 13 and second aperture 14. First aperture 13 is located essentially at the junction where handle portion 12 and finger portion 11 join. Second aperture 14 is located near free end 21 of finger portion 11. As depicted in FIGS. 1 and 2, first aperture 13 and second aperture 14 both extend essentially orthogonal to the longitudinal axis of the portion of flossing device 10 through which they pass. The openings of both apertures are rounded to provide a smooth surface for the flossing material to ride along, thereby avoiding abrasion of the flossing material when it is advanced. The apertures are dimensioned to receive flossing material with a clearance to permit easy threading.

Flossing device 10 may also include friction ribs 16 extending laterally at a position above and/or below the openings 13a and 13b of first aperture 13. They may be provided on either handle portion 12, finger portion 11, or both and on one or both sides of either the handle or finger portions. Therefore, there can be up to four sets of friction ribs 16 on flossing device 10. In place of ribs, laterally extending friction grooves may be provided at one or more locations. Friction ribs 16 aid the user to fix the flossing material 15 by preventing flossing material 15 from sliding relative to handle portion 12 or finger portion 11 due to the frictional engagement between friction ribs 16 and the user's digit, such as a thumb. They can also prevent a digit from sliding along an otherwise smooth surface of the flossing device.

In the first embodiment of FIGS. 1 and 2, the flossing device 10 is essentially straight. As shown in FIGS. 3 and 4, in accordance with a second embodiment of the present invention, flossing device 10' is provided with a finger portion 11' which forms an obtuse angle with handle portion 12'. Furthermore, a first aperture 30 and second aperture 31 are both located on finger portion 11', the first aperture being adjacent the near end 23' of finger portion 11', the second aperture being near the free end 21' of the finger portion. Both apertures extend orthogonal to the longitudinal axis of finger portion 11' through which they pass. This construction also allows for easy manipulation of finger portion 11' within the mouth of the user because of the angled relation between the handle and finger portions. It is also to be understood that an alternate embodiment can be constructed such that first aperture 30 is located on handle portion 12' with the aperture extending orthogonal to the longitudinal axis of finger portion 12'.

Features in FIGS. 3 and 4 similar in structure and operation to features in FIGS. 1 and. 2 are assigned like reference numerals and described.

The finger portion of the embodiments of FIGS. 1–4 is preferably of a length from about one inch to about four inches from the junction of the finger and handle portions. If the finger portion is too short, the user's hand that holds the device must enter the mouth. If the finger portion is too long, it is difficult to control the free end and the device. The entire device is preferably of a length similar to that of conventional toothbrushes, so as to fit in conventional toothbrush cases.

The flossing devices in accordance with the invention of FIGS. 1–4 are preferably free of apertures therethrough intended for receiving the floss material aside from the first and second apertures. Thus, a hole at the end 20 of flossing device 10 might be provided for mounting the device on a hook, but not to receive the floss. The flossing device in accordance with the invention is also preferably free of means for fixing the position of the floss other than by engagement of the floss against the flossing device by the user's hand or digits.

Reference is now made to FIG. 5 which illustrates a third embodiment of the present invention. The dental flossing device, designated generally at 50, has a handle portion 12" and a finger portion 11". Handle portion 12" has a first end 20" and a second end 22". Finger portion 11" has a free end 21" and a near end 23". Near end 23" of finger portion 11" is joined to second end 22" of handle portion 12".

In this third embodiment, there is only one aperture 51 located near free end 21" of finger portion 11". As depicted in FIG. 5, aperture 51 extends essentially orthogonal to the longitudinal axis of finger portion 11". Furthermore, features in FIG. 5, such as the tapering of finger portion 11" and/or handle portion 12", the material flossing device 50 is made from, the cross-sectional shape of flossing device 50, and the dimensions of the finger portion and of the device are similar in structure and operation to corresponding features in FIGS. 1 and 2 and are not repeated herein but it is understood that these features are applicable to the embodiment of FIG. 5.

Flossing device 50 may also include friction ribs 16' extending laterally on either handle portion 12", finger portion 11", or both, and on one or both sides of either the handle or finger portions. It is also understood that there may be one set of friction ribs 16" on either side of the flossing device extending from at least a portion of finger portion 11" to handle portion 12". The device 50 is otherwise free of means to which the floss can be secured to prevent movement relative to the device without being held by the hand of the user.

As in the case of the embodiments of FIGS. 1–4, a hole at first end 20" can be provided for mounting the device on a hook, but not to receive the floss. Also, as in the case of the embodiment of FIGS. 3 and 4, the longitudinal axis of the finger portion 11" of the embodiment of FIG. 5 can be formed at an obtuse angle to the longitudinal axis of the handle portion 12".

A description of the preferred method of using the device of the present invention will now be provided with reference to FIGS. 1–2, the embodiment of FIGS. 3 and 4 operating in a like manner.

A selected length of flossing material 15 is introduced through entrance opening 13a of first aperture 13. Thereafter, flossing material 15 is led up the finger portion and passed through an entrance opening 24 of second aperture 14. The user holds flossing device 10 in a second hand with a digit(s) over first aperture 13, or a set of friction ribs 16 located above first aperture 13, and/or a set of friction ribs 16 over which the flossing material 15 passes as it extends down handle portion 12. Being mindful of not allowing all of flossing material 15 to pass through first aperture 13, the user holds the flossing material near a free end 15' thereof and slowly pulls on flossing material 15 so that there is a sufficient length of flossing material to effect flossing in accordance with one's personal technique of flossing. A sufficient amount of flossing material 15 adjacent free end 15' is needed to be able to grip with a plurality of fingers or to be able to wrap around one finger. The other free end 15" of flossing material 15 is thereafter pressed against handle portion 12 and/or finger portion 11 by the use of the user's digits in order to aid in the restraining of all of flossing material 15 from passing through first aperture 13. The pressure applied by the user's digit(s) to aperture 13 and/or friction ribs 16 should be sufficient to resist movement of the flossing material when held taut during use. The level of pressure required is minimized by taking advantage of the holding force applied to the flossing material as it passes or after it passes through first aperture 13.

It is also to be understood that threading flossing material 15 through first aperture 13 and second aperture 14 can also be accomplished by first threading flossing material 15 through second aperture 14 and thereafter threading flossing material 15 through first aperture 13.

Thereafter, the only necessary remaining step is to place free end 21 of flossing device 10 into the mouth and in accordance with the user's personal preference, move back and forth or up and down, using the present invention in conjunction with the user's fingers of the first hand holding flossing material 15. When an additional length of flossing material is needed, the user merely lessens the pressure of the digit(s) of his or her second hand and pulls the desired additional length with his or her first hand, using the digit pressure to closely control the amount of additional flossing material. The user then reapplies the digit pressure with the second hand, grabs the flossing material with his or her first hand nearer to flossing device 10 and proceeds with flossing.

It is further to be understood that the same method of using the flossing device can be employed in accordance with the second embodiment depicted in FIGS. 3 and 4. In FIGS. 3 and 4, flossing material 15 is either threaded through first aperture 30 and thereafter threaded back through second aperture 31, or flossing material 15 can be first threaded through second aperture 31 and thereafter threaded through first aperture 30. As seen in FIGS. 3 and 4, flossing material 15 can be threaded through first and second apertures 30 and 31 so as to run along either one side 11a' or the other side 11b' of the finger portion.

A description of the method of using the device in accordance with the third embodiment will now be provided with reference to FIG. 5. A selected length of flossing material 15 is introduced through an entrance opening of aperture 51. Thereafter, flossing material 15 is led down a side of the finger portion where free end 15" of flossing material 15 is thereafter pressed against handle portion 12" and/or finger portion 11" by the use of a user's digit of one hand, such as a thumb, in order to restrain all of the flossing material 15 from passing through aperture 51. The pressure applied by the user's digit to free end 15" of flossing material 15 should be sufficient to resist movement of the flossing material when held taut during use. Furthermore, free end 15' of flossing material 15 is provided to effect flossing in accordance with one's personal technique of flossing, keeping in mind that a sufficient amount is needed to be able to grip with a plurality of fingers on the user's other hand or to be able to wrap around one finger of the user's other hand.

Furthermore, flossing material 15 can be threaded through aperture 51 so as to run along either one side 11a" or the other side 11b" of the finger portion.

Lastly, it is also to be understood that the embodiment of FIGS. 3 and 4 can be modified to comprise a handle portion and a finger portion having only one aperture 31 near free end 21' of finger portion 11'.

The method of using the flossing device in accordance with this fourth embodiment would be similar to the method of using the flossing device as illustrated in FIGS. 3 and 4, except to the extent that free end 15" of flossing material 15 is pressed against either handle portion 12' and/or finger portion 11' by the use of the user's digit, such as a thumb on the hand holding the stick member.

It will thus be seen that the objects set forth above, among those made apparent from the preceding description, are efficiently attained and, since certain changes may be made in the above constructions without departing from the spirit and scope of the invention, it is intended that all matter contained in the above description shall be interpreted as illustrative and not in a limiting sense.

By the device and method in accordance with the invention, an improved flossing tool is provided which is easy to use and easy to carry and store, while permitting effective flossing.

It is also to be understood that the following claims are intended to cover all of the generic and specific features of the invention herein described and all statements of the scope of the invention which, as a matter of language, might be said to fall therebetween.

What is claimed is:

1. A device for flossing teeth, comprising:
a length of floss having first and second ends;
an elongated stick member having a handle portion and a finger portion;
said handle portion having a first end and a second end;
said finger portion having a near end and a free end, said near end of said finger portion being connected to said second end of said handle portion, said stick member having a first side and a second side opposite said first side, said sides being intermediate said first end of said handle portion and said free end of said finger portions;
said stick member having a first aperture dimensioned to receive said floss, essentially positioned near the connection of said near end of said finger portion and said second end of said handle portion, said first aperture extending from said first side of said stick member to said second side of said stick member and essentially orthogonal to the longitudinal axis of the portion of said stick member through which it passes;
said finger portion having a second aperture positioned adjacent said free end of said finger portion dimensioned to receive said floss, said second aperture extending essentially orthogonal to the longitudinal axis of said finger portion from said first side of said stick member to said second side of said stick member, said length of floss being freely displaceable through said first and second apertures except when said floss is engaged against said stick member by the hand of the user holding the handle member, said length of floss extending from its first end through said second aperture from said first to said second side of said stick member, along said second side of said finger portion of said stick member and through said first aperture from second to said first side of said stick member to its second end, the portion of said length of floss between said second aperture and said first end of said length of floss being free of connection to said stick member to permit said length of floss to be pulled from said first side of said stick member from said second aperture.

2. The device for flossing teeth, as claimed in claim 1, wherein said stick member includes friction means on said second side of said stick member for engagement of said floss by said hand of the user to prevent free displacement of said floss through said apertures.

3. The device for flossing teeth, as claimed in claim 2, wherein said friction means is positioned between said free end of said finger portion and said first aperture.

4. The device for flossing teeth, as claimed in claim 2, wherein said friction means comprises a plurality of laterally extending ribs.

5. The device for flossing teeth, as claimed in claim 2, wherein said friction means is provided on opposed sides of said first aperture as viewed along the length of said stick member.

6. The device for flossing teeth, as claimed in claim 2, wherein said finger portion is thinner in cross-sectional area at least in the region thereof extending from said free end thereof than the region of said stick member adjacent the near end of said finger portion.

7. The device for flossing teeth, as claimed in claim 6, wherein said stick member is formed from a material selected from the group consisting of plastic, wood, metal and rubber.

8. The device for flossing teeth, as claimed in claim 1, wherein said stick member includes friction means on said first side of said stick member for engagement of said floss by said hand of the user to prevent free displacement of said floss through said apertures.

9. The device for flossing teeth, as claimed in claim 1, wherein said handle portion is essentially tapered from its second to its first end.

10. The device for flossing teeth, as claimed in claim 1, wherein said finger portion is thinner in cross-sectional area at least in the region thereof extending from said free end thereof than the region of said stick member adjacent the near end of said finger portion.

11. The device for flossing teeth, as claimed in claim 10, wherein said finger portion is sufficiently flexible to permit said finger portion to flex at least a small distance in response to said floss being pulled from said first side of said stick member from said second aperture while said stick member is held by a user by said handle portion and a region of said floss is held against said stick member by the user to prevent relative displacement of the floss relative to the stick member.

12. The device for flossing teeth, as claimed in claim 10, wherein said stick member is free of apertures intended for receipt of floss therethrough except for said first and second apertures.

13. The device for flossing teeth, as claimed in claim 1, wherein said finger portion is sufficiently flexible to permit said finger portion to flex at least a small distance in response to said floss being pulled from said first side of said stick member from said second aperture while said stick member is held by a user by said handle portion and a region of said floss is held against said stick member by the user to prevent relative displacement of the floss relative to the stick member.

14. The device for flossing teeth, as claimed in claim 1, wherein said stick member is formed from a material selected from the group consisting of plastic, wood, metal and rubber.

15. The device for flossing teeth, as claimed in claim 1, wherein said stick member is free of apertures therethrough intended for receipt of floss therethrough except for said first and second apertures.

16. The device for flossing teeth, as claimed in claim 1, wherein each of said first and second apertures has ends which are rounded in the direction of the length of the apertures toward adjacent surfaces of said finger portion.

17. The device for flossing teeth, as claimed in claim 1, wherein said finger portion is of a length from about one inch to about four inches.

18. The device for flossing teeth, as claimed in claim 1, wherein said handle portion has a longitudinal axis and said finger portion has a longitudinal axis, said longitudinal axis of said handle portion and said longitudinal axis of said finger portion forming an obtuse angle.

19. The device for flossing teeth, as claimed in claim 18, wherein said stick member includes friction means on said second side of said stick member for engagement of said floss by the hand of the user to prevent free displacement of said floss through said apertures.

20. The device for flossing teeth, as claimed in claim 19, wherein said friction means is provided on opposed sides of said first aperture as viewed along the length of said stick member.

21. The device for flossing teeth, as claimed in claim 18, wherein said finger portion is thinner in cross-sectional area at least in the region thereof extending from said free end thereof than the region of said stick member adjacent the near end of said finger portion.

22. The device for flossing teeth, as claimed in claim 21, wherein said stick member includes friction means on said second side of said stick member for engagement of said floss by the hand of the user to prevent free displacement of said floss through said apertures.

23. The device for flossing teeth, as claimed in claim 21, wherein said finger portion is sufficiently flexible to permit said finger portion to flex at least a small distance in response to said floss being pulled from said first side of said stick member from said second aperture while said stick member is held by a user by said handle portion and a region of said floss is held against said stick member by the user to prevent relative displacement of the floss relative to the stick member.

24. The device for flossing teeth, as claimed in claim 18, wherein said stick member includes friction means on said first side of said stick member for engagement of said floss by of the user to prevent free displacement of said floss through said apertures.

25. The device for flossing teeth, as claimed in claim 18, wherein each of said first and second apertures has ends which are rounded in the direction of the length of the apertures toward adjacent surfaces of said finger portion.

26. The device for flossing teeth, as claimed in claim 18, wherein said finger portion is of a length from about one inch to about four inches.

27. A device for flossing teeth, comprising:
a length of floss having first and second ends;
an elongated stick member having a handle portion and a finger portion;
said handle portion having a first end and a second end;
said finger portion having a near end and a free end, said near end of said finger portion being connected to said second end of said handle portion, said stick member having a first side and a second side opposite said first side, said sides being intermediate said first end of said handle portion and said free end of said finger portions;
said finger portion having a single aperture positioned essentially adjacent said free end of said finger portion dimensioned to receive said length of floss, said aperture extending from said first side of said stick member to said second side of said stick member and essentially orthogonal to the longitudinal axis of said finger portion, said length of floss being freely displaceable through said aperture, said length of floss extending from its first end through said aperture from a first to a second side of said stick member and along at least a portion of said second side of said stick member to its second end to permit said floss to be pulled from said first side of said stick member, said stick member including a region on a side thereof against which said floss can be pressed by the hand of a user holding said handle portion, said stick member being otherwise free of apertures therethrough designed to receive floss and free of means to which said floss can be secured to prevent movement relative to said stick member without being held by the hand of the user.

28. The device for flossing teeth, as claimed in claim 27, wherein said stick member includes friction means on at least said second side of said stick member for engagement of said floss by the hand of the user to prevent free displacement of said floss through said aperture.

29. The device for flossing teeth, as claimed in claim 28, wherein said stick member includes said friction means on both said first and second sides of said stick member.

30. The device for flossing teeth, as claimed in claim 27, wherein said finger portion is sufficiently flexible to permit said finger portion to flex at least a small distance in response to said floss being pulled from said first side of said stick member from said aperture while said stick member is held by a user by said handle portion and a region of said floss is held against said stick member by the user to prevent relative displacement of the floss relative to the stick member.

31. The device for flossing teeth, as claimed in claim 27, wherein said stick member is formed from a material selected from the group consisting of plastic, wood, metal and rubber.

32. The device for flossing teeth, as claimed in claim 27, wherein said finger portion is thinner in cross-sectional area at least in the region thereof extending from said free end thereof than the region of said stick member adjacent the near end of said finger portion.

33. The device for flossing teeth, as claimed in claim 27, wherein said handle portion has a longitudinal axis and said finger portion has a longitudinal axis, said longitudinal axis of said handle portion and said longitudinal axis of said finger portion forming an obtuse angle.

34. A method for flossing teeth comprising:
providing an elongated stick member having a handle portion and a finger portion, said handle portion having a first end and a second end, said finger portion having a near end and a free end, said near end of said finger portion being connected to said second end of said handle portion, said finger portion having a first aperture dimensioned to receive floss, essentially positioned near the connection of said near end of said finger portion and said second end of said handle portion, said first aperture extending essentially orthogonal to the longitudinal axis of said stick member, said finger portion having a second aperture positioned essentially at said free end of said finger portion dimensioned to receive floss, said second aperture extending essentially orthogonal to the longitudinal axis of said finger portion;

threading a length of floss through one of said first and second apertures from a first to a second side of said stick member, along said second side of said finger portion of said stick member and through said other of said first and second apertures from said second to said first side of said stick member;

providing a sufficient length of floss extending from said second aperture to permit grasping by a first hand of a user at a position spaced from said second aperture and grasping same while holding said handle portion in a second hand of the user;

clamping by the second hand of the user at least one of the portion of said floss between said first aperture and said second aperture and the portion of said floss extending from said first aperture, against a side of said stick member; and performing flossing by inserting the free end of said finger portion into the mouth of the user and moving the portion of said floss between said first hand and said second aperture by manipulation of said first and second hands.

35. The method of claim 34, wherein said clamping step is performed by a digit of said second hand of said user.

36. The method of claim 35, and including the further step of releasing the clamping of said floss by the second hand of said user, pulling an additional length of floss through the second aperture by the first hand of the user, grasping said pulled floss at a position spaced from said second aperture and reclamping the portion of said floss extending from said first aperture against said stick member.

37. A method for flossing teeth comprising:

providing an elongated stick member having a handle portion and a finger portion, said handle portion having a first end and a second end, said finger portion having a near end and a free end, said near end of said finger portion being connected to said second end of said handle portion, said stick member having a first side and a second side opposite said first side, said sides being intermediate said first end of said handle portion and said free end of said finger portions;

said finger portion having an aperture positioned essentially at said free end of said finger portion dimensioned to receive floss, said aperture extending essentially orthogonal to the longitudinal axis of said finger portion from said first side of said stick member to said second side of said stick member;

threading a length of floss through said aperture between said first and said second sides of said stick member;

providing a sufficient length of floss extending from said aperture at said first side of said stick member to permit grasping by a first hand of a user at a position spaced from said aperture and grasping same while holding said handle portion in a second hand of the user;

providing a sufficient further length of floss extending from said aperture at said second side of said stick member to permit manual clamping of said length of floss against said stick member;

clamping by the second hand of the user a portion of said further length of floss extending from said aperture against said stick member, leaving said floss otherwise free of connection to said stick member; and performing flossing by inserting the free end of said stick member into the mouth of the user and moving the portion of said floss between said first hand and said aperture by manipulation of said first and second hands.

38. The method of claim 37, wherein said clamping step is performed by a digit of said second hand of said user.

39. The method of claim 38, and including the further step of releasing the clamping of said floss by the second hand of said user, pulling an additional length of floss through said aperture by the first hand of the user, grasping said pulled floss at a position spaced from said aperture and manually reclamping the portion of said floss extending from said aperture against said stick member.

* * * * *